United States Patent [19]

Smith et al.

[11] Patent Number: 4,889,530
[45] Date of Patent: * Dec. 26, 1989

[54] WOUND DRESSING CONTAINING ACRYLATE OR METHACRYLATE HYDROGEL POLYMER

[75] Inventors: Daniel J. Smith, Stow; Sanjay R. Patel, Akron, both of Ohio

[73] Assignee: University of Akron, Akron, Ohio

[*] Notice: The portion of the term of this patent subsequent to Nov. 1, 2005 has been disclaimed.

[21] Appl. No.: 223,086

[22] Filed: Jul. 22, 1988

Related U.S. Application Data

[62] Division of Ser. No. 915,545, Oct. 6, 1986, Pat. No. 4,781,921.

[51] Int. Cl.$^4$ .............................................. A61F 13/00
[52] U.S. Cl. ..................................................... 604/304
[58] Field of Search ............... 604/372, 304, 287, 292, 604/293, 303, 304, 307, 308

[56] References Cited

U.S. PATENT DOCUMENTS

4,671,267 6/1987 Stout .................................. 604/308
4,781,921 11/1988 Smith et al. ........................... 424/81

OTHER PUBLICATIONS

Kickhoefen, B. et al., Biomaterials, vol. 7, pp. 67–72, (1986).

*Primary Examiner*—Joseph L. Schofer
*Assistant Examiner*—Peter F. Kulkosky
*Attorney, Agent, or Firm*—Olham & Oldham Co.

[57] ABSTRACT

Acrylate and methacrylate monoesters and diesters having the following formula (I)

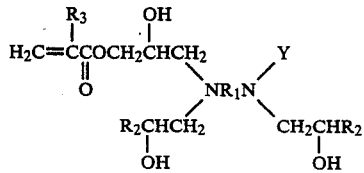

wherein $R_1$, $R_2$, $R_3$ are as defined in the specification, are disclosed. These monomers are polymerizable into hydrogen polymers which are extremely hydrophilic. These hydrogel polymers are useful in the preparation of wound dressings. These polymers form complexes with polyvalent metal ions such as Ca, Mg, Mn and Cu, and possess macrophage stimulating activity in addition to the useful properties possessed by other acrylate and methacrylate hydrogel polymers.

6 Claims, No Drawings

WOUND DRESSING CONTAINING ACRYLATE OR METHACRYLATE HYDROGEL POLYMER

This is a division of co-pending application Ser. No. 915,545 filed Oct. 6, 1986, now U.S. Pat. No. 4,781,921.

TECHNICAL FIELD

This invention relates to acrylate and methacrylate monoesters and diesters of cetain diaminopolyhydroxy compounds, and to hydrogels prepared therefrom.

BACKGROUND ART

Quadrol, N,N,N',N'-tetrakis(2-hydroxypropyl)ethylenediamine, is often used as a cross-linking agent and catalyst in the synthesis of urethane foams and as an analytical reagent for the quantitative determination of $Mn^{3+}$. Quadrol forms complexes with other polyvalent metal ions, e.g., cobalt, copper (II) and zinc. Recently applicants and coworkers have found that Quadrol possesses immunological activity. When mouse macrophages are exposed to Quadrol in vitro, the macrophages are rapidly stimulated as measured by increased phagocytosis and spreading. This stimulation was shown to be both time and concentration dependent. These findings were reported in M. V. Bhide et al, *Journal of Immunopharmacology*, vol. 7, no. 3, pp. 303-312 (1985).

Quadrol can be prepared by reacting one mol of ethylenediamine with 4 mols of propylene oxide as described in U.S. Pat. No. 2,697,113 to Lundsted et al.

U.S. Pat. No. 3,868,409 discloses, inter alia, the monomers obtained by reacting either 3 or 4 moles of glycidyl methacrylate with ethylenediamine, and polymers thereof. The monomers are trifunctional or tetrafunctional, depending on the number of moles of glycidyl methacrylate reacted, and are capable of a high degree of cross-linking. Polymers formed from these monomers are highly cross-linked, rigid and brittle. Also disclosed are other polymers formed by reaction of glycidyl methacrylate and other epoxy compounds with various monoamines, diamines and polyamines. Patentee characterizes his polymers as having exceptionally high strength, and as bonding strongly to metals.

Hydrogel polymers of certain methacrylate monomers, notably 2-hydroxyethyl methacrylate (HEMA), are well known. HEMA polymers are widely used in the manufacture of contact lenses and also have been reported as being useful in other biomedical and surgical applications. HEMA is capable of homopolymerizing and copolymerizing with other methacrylates to form three-dimensional hydrophilic polymer (hydrogel) networks. References disclosing HEMA polymers include, for example, D. E. Gregonis et al., "Hydrogels For Medical And Related Applications", American Chemical Society Symposium, Series No. 31, edited by J. D. Andrade, August 1976, pages 88-104, and M. F. Refojo et al, *Journal of Applied Polymer Science*, vol. 9, pages 2425-2435 (1965). M. F. Refojo, *J. Applied Polymer Sci.*, vol. 9, pp 3161-3170 (1965) discloses hydrogels prepared from glyceryl methacrylate.

U.S. Pat. No. 3,220,960 to Wichterle et al discloses hydrogels consisting essentially of 20-97 percent of an aqueous liquid and a cross-linked hydrophilic polymer. Use for hydrogels obtained from various derivatives of acrylic and methacrylic acids include dialysis membranes, diaphragms, contact lenses and other uses where prolonged contact with body tissues is required.

Wound dressings incorporating certain hydrogels have been described in the literature. Agar-acrylamide hydrogels and their use in wound dressings are described, for example in B. Kickhoefer et al., *Biomaterials*, vol. 7, pages 67-72 (1986).

DISCLOSURE OF THE INVENTION

An object of this invention is to provide novel monofunctional and bifunctional acrylate and methacrylate monomers which are polymerizable into hydrogel polymers.

Another object of this invention is to provide novel acrylate and methacrylate hydrogel polymers.

A more specific object of this invention is to provide novel acrylate and methacrylate hydrogel polymers which are useful in biomedical applications.

The novel monomers of this invention have the following formula (I)

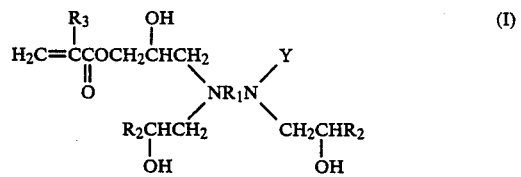

wherein $R_1$ is a divalent hydrocarbon radical containing from 2 to about 6 carbon atoms; $R_2$ is hydrogen, methyl or ethyl; $R_3$ is hydrogen or methyl; and Y is

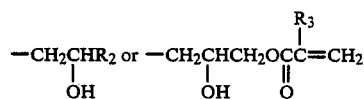

In preferred embodiments of this invention, $R_1$ is ethylene (i.e. $-CH_2CH_2-$), $R_2$ and $R_3$ are methyl, and Y is

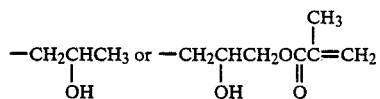

The novel polymers of this invention are hydrogel polymers (including copolymers) of the novel monomers described above.

Hydrogel polymers of this invention are biologically active; in particular they possess macrophage stimulation activity. As a consequence, these polymers are useful as wound dressings. The polymers of this invention are useful as chelating agents for polyvalent metal ions, such as copper, calcium, magnesium, manganese and zinc. These as sustained and controlled for release devices, e.g., release of metal ions and medications into wounds.

BEST MODE FOR CARRYING OUT INVENTION

The monomers of this invention may be either monofunctional or bifunctional, i.e., they may have either one or two acrylate or methacrylate groups per molecule.

Monofunctional monomers may be prepared by a first general method, and bifunctional monomers by a second general method as will now be described in detail.

The first reaction step in preparing both monofunctional and bifunctional monomers is to react an aliphatic diamine having the formula (II)

$$H_2NR_1NH_2 \quad (II)$$

with an alkylene oxide having the formula (III)

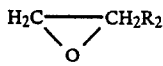
(III)

thereby forming an N,N'-bis(2-hydroxyalkyl) alkylenediamine compound of the formula (IV)

(IV)

The aliphatic diamines of the formula (II) contain from 2 to about 6 carbon atoms. The nitrogen atoms are attached to different carbon atoms, preferably to the two end carbon atoms, in which case $R_1$ is a straight chain alkylene group. Suitable aliphatic diamines include ethylenediamine, propylenediamine (1,2-diaminopropane), trimethylenediamine (1,3-diaminopropane), tetramethylenediamine (1,4-diaminobutane), 1,3-diamino-1-methylpropane, 1,3-diamino-2-methylpropane, pentamethylenediamine (1,5-diaminopentane), 1,4-diamino-1-methylbutane, 1,4-diamino-2-methylbutane, 1,3-diamino-2,2-dimethylpropane hexamethylenediamine (1,6-diaminohexane), 1,4-dimethylbutane, and 1,3-diamino-1,1,2-trimethylpropane. The preferred aliphatic diamine is ethylenediamine.

Suitable alkylene oxides of the formula (III) are ethylene oxide, propylene oxide (which is preferred), and butylene oxide.

The reaction between the aliphatic diamine and the alkylene oxide may be carried out by adding the latter dropwise to the former, either neat or in a suitable solvent such as absolute ethanol. The reaction temperature may range from about 20° C. up to the boiling point of the amine (if neat) or solution, and may exceed the boiling point of the alkylene oxide. The materials react in stoichiometric proportions; thus, two mols of alkylene oxide per mol of aliphatic diamine are required.

When propylene oxide is reacted with ethylene diamine, the reaction product is N,N'-bis-(2-hydroxypropyl)ethylenediamine, (IV-a), which is the preferred compound of the formula (IV).

The second step in the preparation of monoacrylates and monomethacrylates according to the first general method is to react the compound of the formula (IV) with a further quantity of alkylene oxide (III) thereby forming an N,N,N'-tris(2-hydroxyalkyl)alkylenediamine of the following formula (V)

(V)

The alkylene oxide used in this step may be the same as or different from the alkylene oxide used in the first step. Preferably the same alkylene oxide is used in both steps. The alkylene oxide may be added dropwise to a solution of the disubstituted diamine (IV) until the stoichiometric quantity, which is one mol of alkylene oxide per mol of disubstituted diamine (IV), has been added. An inert solvent, e.g., a mixed solvent consisting of absolute ethanol, methanol and water, may be used. The reaction temperature may range from about 20° C. up to the boiling point of the solution, although an elevated temperature is preferred. After addition of the alkylene oxide is complete, the reaction mixture may be cooled and the product (V) separated from unreacted disubstituted diamine (IV) by conventional means.

Reaction of N,N'-bis(2-hydroxypropyl)ethylenediamine (IV-a) with propylene oxide yields N,N,N'-tris(2-hydroxypropyl)ethylenediamine (V-a).

It is desirable to prepare the trisubstituted diamine (V) indirectly from a disubstituted diamine (IV) instead of directly from an aliphatic diamine (II) because of the difficulty in separating by-products. For example, N,N,N'-tris-(2-hydroxypropyl)ethylenediamine (V-a) should be synthesized in two steps via N,N'-bis(2-hydroxypropyl)ethylenediamine (IV-a) rather than directly form ethylenediamine, because of the difficulty in the separation of side reaction products and unreacted N,N'-bis(2-hydroxypropyl)ethylenediamine from the trisubstituted produce (V-a).

The final step in the first general method is to react the trisubstituted diamine (V) with either glycidyl acrylate or methacrylate to form the product monoacrylate or monomethacrylate, which has the following formula (VI)

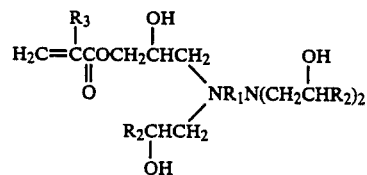
(VI)

Glycidyl methacrylate is ordinarily preferred, since in general the preferred hydrogel polymers are the methacrylates.

Reaction of the trisubstituted diamine (V) with glycidyl acrylate or methacrylate may be carried out by adding the latter to the former at ambient temperature. The reaction is carried out in an inert solvent, e.g. methylene dichloride or methanol.

It is desirable to add a polymerization inhibitor, e.g. 4-methoxyphenol, to the reaction medium. The product (VI) may be recovered from the reaction mixture by conventional means.

In a preferred embodiment according to the first general method, N,N,N'-tris(2-hydroxypropyl)ethylenediamine (V-a) is reacted with glycidyl methacrylate to form Quadrol methacrylate (VI-a).

The first step in the preparation of diacrylates and dimethacrylates according to the second general method is to prepare a disubstituted diamine (IV) from an aliphatic diamine (II) and an alkylene oxide (III) as above described. In particular, N,N'-bis(2-hydroxypropyl)ethylenediamine (IV-a) may be prepared from ethylenediamine and propylene oxide.

The second and final step in the second general method is to react the disubstituted diamine (IV) with ether glycidyl acrylate or glycidyl methacrylate, depending on whether a diacrylate or a dimethylacrylate is desired. Suitable solvents and reaction conditions are generally similar to those used in the analogous preparation of monoacrylates and monomethacrylates (VI) from a trisubstituted diamine (V), although a slightly lower temperature, e.g. about 20° C., may be maintained while the glycidyl acrylate or methacrylate is being added. The product diacrylate or dimethacrylate has the following formula (VII)

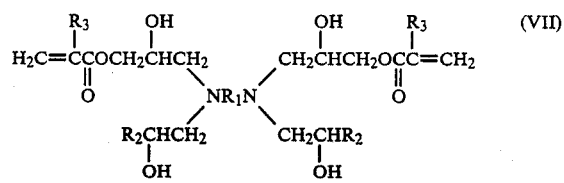

In a preferred embodiment according to the second general method, glycidyl methacrylate is added to a solution of N,N'-bis(2-hydroxypropyl)ethylenediamine (IV-a) to form Quadrol dimethacrylate (VII-a).

It will be noted that the monomers of the general formula (I) include the monofunctional monomers of the formula (VI) and the difunctional monomers of the formula (VII).

It will also be noted that both the monoacrylates and monomethacrylates of the formula (VI) and the diacrylates and dimethacrylates of the formula (VII) are prepared by reaction of the corresponding substituted alkylenediamine of the formula (VIII)

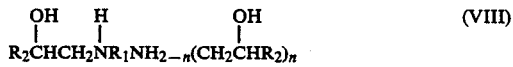

when n is 1 or 2, with either glycidyl acrylate or glycidyl methacrylate. It will also be noted that formula (VIII) embraces formulas (IV) and (V), the formula (IV) compounds being those of formula (VIII) wherein n=1, and the formula (V) compounds being those of formula (VIII) wherein n=2.

Acrylate and methacrylate monomers of this invention are soluble in water and common organic solvents. Thus, Quadrol methacrylate and Quadrol dimethacrylate are soluble in water, ethanol, ether and methylene dichloride. The water solubility of these monomers is highly advantageous in carrying out aqueous phase polymerizations.

Monomers of this invention are polymerizable in the presence of a conventional polymerization initiator, e.g. a redox catalyst or a free radical initiator, either in aqueous solution or in bulk. The amount of monomer can range from about 20 percent to nearly 100 percent of the total weight of the polymerization medium. Conventional redox catalysts, e.g. a redox catalyst system of ammonium persulfate and sodium metabisulfite, can be used for solution polymerization. The amount of catalyst required is small, usually less than 2 percent by weight based on the total weight of reaction medium. A small amount of a polymerization initiator (or free radical initiator), e.g. tetrabutylperoxypivalate or azobis(isobutyronitrile) (AIBN) may be advantageously used in lieu of a redox catalyst in bulk polymerization or in polymerization in an organic solvent. Monomers of this invention may be autocatalytic.

Monofunctional monomers of this invention (formula VI) can be homopolymerized, copolymerized with one or more additional monofunctional comonomers (2-hydroxyethyl methacrylate, for example), or cross-linked. The cross-linking agent can be a bifunctional monomer of this invention (formula VII) and in particular Quadrol dimethacrylate (VII-a). Conventional cross-linking agents, such as tetraethyleneglycol dimethacrylate, can also be used. An advantage of using a bifunctional monomer of this invention and in particular Quadrol dimethacrylate is the greater hydrophilicity of the resulting hydrogel polymers. Polymers of Quadrol methacrylate cross-linked with Quadrol dimethacrylate, for example, are more hydrophilic than polymers of Quadrol methacrylate cross-linked with tetraethylene glycol dimethacrylate. Greater water solubility allows the use of higher monomer concentrations in an aqueous polymerization medium without sacrificing clarity in the polymer product. The amount of cross-linking agent when used is usually no more than about 5 percent by weight, based on total monomer content, and is more usually about 2 percent to about 4 percent by weight, based on total monomer content. Conventional polymerization conditions used for preparation of known methacrylate hydrogel polymers can be used herein.

Non-cross-linked polymers of this invention are water-soluble; cross-linked polymers of this invention are in the form of hydrogels.

Polymers of this invention, whether cross-linked or not, as extremely hydrophilic. For example, poly(Quadrol methacrylate) hydrogel, cross-linked with 4 percent by weight of tetraethylene glycol dimethacrylate, after equilibration with water, contains between 80 percent and 85 percent by weight of water. Poly(Quadrol dimethacrylate) hydrogel, also cross-linked with 4 percent by weight of tetraethyleneglycol dimethacrylate, contains over 90 percent by weight of water at equilibrium.

Polymers of this invention are also non-toxic.

Non-cross-linked polymers of this invention are chelating agents. They form complexes with polyvalent metal ions, such as copper, calcium, magnesium, manganese and zinc. For example, poly(Quadrol methacrylate) forms a 1:1 (mol ratio) complex with the cupric ion. The metal ions can be completely removed from these complexes by dialysis with an appropriate material such as a buffered EDTA (ethylenediamine tetraacetic acid) solution.

Polymers of this invention are biologically active. In particular, they have macrophage stimulation activity. In other words, the polymers of this invention stimulate the activity of macrophages in the bodies of humans and other warm blooded animals, so that they more effectively perform their functions, for example, that of removing and consuming bacteria and other foreign bodies in the body of the host animal. Cross-linked polymers of this invention are particularly useful in biomedical applications because of their physical form; as hydrogels they swell but do not dissolve in water.

Polymers of this invention, especially cross-linked polymers, are useful as wound dressings. They may be applied to the skin of the animal at the wound or lesion site in the same way as polymeric wound dressings now known. By virtue of their macrophage stimulation activity, polymeric wound dressings of this invention stimulate the activity of macrophages at the wound site, thereby accelerating wound healing. Furthermore, the invention wound dressings perform their function without being absorbed into the bloodstream of the host. As a consequence, there are no side reactions and a dressing can remain in place for a long period of time, with changes only at infrequent intervals. In contrast, presently known wound dressings merely protect the wound from infection and foreign matter (a function which the invention wound dressings also perform) and (where desired) serve as carriers for pharmacological agents without having any biological activity of their own.

These polymers may also be used as carriers for biologically active agents. For example, biologically important metal ions such as calcium, magnesium, manganese or zinc may be supplied to a wound by preparing a polymer/metal ion complex as above described, placing this complex over the wound, and supporting the complex with a conventional bandage. The metal ion is released gradually and in a controlled basis into the wound. Other controlled release wound dressings can be prepared in a similar manner. The only requirement is that the biologically active material must be absorbable by the polymer and slowly releasable therefrom.

Polymers of this invention can also be formed into soft contact lenses. These polymers, incorporating a biologically active agent, are particularly useful for controlled release of a medication into the eye.

Polymers of this invention are also useful for the same purposes as presently known methacrylate hydrogel polymers such as 2-hydroxypropyl methacrylate.

Copolymers of this invention (e.g., a copolymer of Quadrol methacrylate and a hydrophilic comonomer such as 2-hydroxyethyl methacrylate, with or without a cross-linking agent) in general have the same utilities as the corresponding invention homo polymers.

Bifunctional monomers of this invention are particularly useful as cross-linking agents for hydrophylic monofunctional monomers, including monomers of this invention (Quadrol methacrylate, for example) as well as known monomers (e.g., 2-hydroxyethyl methacrylate). They are used in small amounts, typically about 2 to 5 percent by weight, based on total monomer weight. An advantage of cross-linking a monofunctional monomer of this invention (e.g., Quadrol methacrylate) with a bifunctional monomer of this invention (e.g., Quadrol dimethacrylate) rather than a conventional bifunctional monomer (e.g., tetraethyleneglycol dimethacrylate) is that higher monomer solids contents can be used in aqueous polymerization, due to greater hydrophilicity of the cross-linked polymer present as polymerization proceeds. These difunctional monomers can also be used as starting materials for homopolymerization or for copolymerization with known monofunctional or difunctional hydrophilic monomers, e.g. 2-hydroxyethyl methacrylate and tetracthylene glycol dimethacrylate, respectively.

A particularly desirable characteristic of the polymers of this invention is that their actual and potential uses go beyond those of presently known hydrogel polymers. Varius biomedical applications have been particularly noted in this regard.

The invention will now be described further with respect to specific embodiments thereof, as illustrated in the examples which follow. All parts are by weight unless otherwise indicated.

EXAMPLE 1

N,N'-Bis(2-hydroxypropyl)ethylenediamine (IV-a): Propylene oxide (142.4 g, 2.4 mol) was added dropwise over a period of 11 hours to a solution of ethylenediamine (71.9 g, 1.2 mol) in 25 mL absolute ethanol and 10 mL of nitrogen purged distilled water at 90° C. After addition, the reaction was maintained for an additional hour, then cooled to room temperature (about 20° C.). The reaction solution was concentrated by rotary evaporation to give a milky white suspension which, upon dissolution in anhydrous ether, produced a white precipitate of N,N'-bis(2-hydroxypropyl)ethylenediamine in 28.5 percent yield. The product was crystallized from methanol/ethanol [m.p. 132° C., IR(Nujol): 3250(OH); NMR(MeOHd$_4$): $\delta$3.8(m,2H); 2.6(t,8H); 1.2(d,6H)].

EXAMPLE 2

N,N,N'-tris(2-hydroxypropyl)ethlenediamine (V-a): Propylene oxide (181.6 g, 0.3 mol) in 25 mL of absolute ethanol was added dropwise for 4.5 hours to a solution of N,N'-bis(2-hydroxypropyl)ethylenediamine (IV-a) (55 g, 0.3 mol) in 50 mL each of absolute ethanol, methanol and distilled water at 80° C. The reaction mixture was cooled and concentrated to give a milky white viscous suspension. The suspension was dissolved in ether and dried over anhydrous sodium sulfate. Unreacted (IV-a) precipitated and was removed by filtration. Ether was removed from the clear filtrate to produce a viscous liquid. Fractional distillation of the oil produced N,N,N'-tris(2-hydroxypropyl)ethylenediamine[bp. 140° C. at 0.15 mm; yield 55 percent; IR(neet); 3350(broad OH); NMR(CDCl$_3$): $\delta$ 3.8(broad m,3H); 2.5(broad m,10H); 1.1(d,9H)].

EXAMPLE 3

Quadrol methacrylate (VI-a):

Glycidyl methacrylate (5.0 g, 35.5 mmol) was added, dropwise, to a solution of N,N,N'-tris(2-hydroxypropyl)ethylenediamine(V-a) (8.3 g, 35.5 mmol) in 10 mL of CH$_2$Cl$_2$ at room temperature. 4-Methoxyphenol(0.03 g) was added to prevent polymerization. The reaction was maintained for 72 hours at room temperature, then warmed to 30° C. for an additional 24 hours. The reaction was followed by TLC(4 percent MeOH in CCl$_4$; glycidyl methacrylate R$_f$0.69). Quadrol methacrylate (VI-a) was obtained in quantitative yield after removal of the solvent. The product was further purified by dissolving 5 g of (VI-a) in 200 mL distilled water followed by addition of sodium chloride to saturation. The product, which separated out as an oil, was collected, dissolved in CH$_2$Cl$_2$, and dried over anhydrous magnesium sulfate. After filtration, the solvent was removed to give Quadrol-methacrylate [yield, 53 percent; IR(neet):3350(broad OH); 1720(C=O); 1640(C=); NMR(CDCl$_3$): $\delta$6.2(s, 1H); 5.6(s,1H); 4.0(broad m,6); 2.5(broad m,12H); 2.0 (s,3H); 1.1(d,9H)].

EXAMPLE 4

Quadrol dimethacrylate (VII-a):

Glycidyl methacrylate (4.8g, 34 mmol) and 4-methoxyphenol (0.13 g) were added to a solution of N,N'-bis-(2-hydroxypropyl)ethylenediamine (IV-a) (3.0 g, 17 mmol) in 80 mL of methanol at 0° C. The mixture was brought to room temperature and maintained for eight days, followed by heating for 24 hours at 30° C. A quantitative yield of a viscous, slightly brown liquid was obtained after removal of the solvent. The product was further purified by dissolving the liquid in water followed by the addition of sodium chloride to saturation. The oil layer was separated, dissol ved in CH$_2$Cl$_2$ and dried over magnesium sulfate. Filtration and removal of solvent yielded Quadrol dimethylacrylate (VII-a) [yield 48 percent: IR(neet):3350(broad OH); 1700 (C=O); 1620(C=C); NMR (CDCl$_3$): $\delta$6.1(s,2H);

5.6(s,2H); 3.8(broad m,8H); 2.6(broad m,12); 2.0(s,6H); 1.1(d,6H)].

EXAMPLE 5

20 parts of Quadrol methacrylate (VI-a) were dissolved in 78.4 parts of distilled water in a glass mold. This solution was polymerized at room temperature (about 25° C.) in the presence of a redox catalyst system containing 0.8 parts of ammonium persulfate and 0.8 parts of sodium m-bisulfite. After thorough mixing, the solution was degassed twice and finally put into a vacuum oven for 12 hours at room temperature. The clear, tacky polymer was post heated at 55°-60° C. for 24 hours before use.

EXAMPLE 6

65.0 parts of Quadrol dimethacrylate (VI-a), 27.2 parts of distilled water and 2.6 parts of tetrethyleneglycol methacrylate were mixed in a glass mold. The homogenous solution was polymerized using a redox catalyst system containing 2.6 parts of ammonium persulfate and 2.6 parts of sodium m-bisulfite as described in example 5.

EXAMPLE 7

95.7 parts of Quadrol dimethacrylate (VI-a) were mixed with 3.8 parts of cold tetraethyleneglycol methacrylate in a glass mold. This slightly viscous solution was bulk polymerized at room temperature by mixing with 0.47 parts of cold tetrabutylperoxypivalate. The water equilibrated polymer had a physical form similar to that of a soft contact lens.

EXAMPLE 8

35.8 parts of Quadrol methacrylate were dissolved in 63.4 parts of cold distilled water. This solution was mixed with various amounts of tetraethyleneglycol dimethacrylate ranging from 0.35 parts to 4.1 parts. The polymerizations were carried out using redox catalyst system containing 0.72 parts of ammonium persulfate. The tacky hydrogels, upon equilibration with water gave hydrated hydrogels containing 90 to 96 percent by weight water.

Example 8 was repeated using 66.7 parts of Quadrol methacrylate, and 2 or 4 parts of tetraethylene glycol, and 33.3 parts of water as the starting solution. The resulting hydrogels contained about 83 to 86 percent by weight of water.

EXAMPLE 9

15.9 parts of 2-hydroxyethyl methacrylate, 47.8 parts by of Quadrol methacrylate (VI-a) and 1.2 parts of tetrethyleneglycol dimethacrylate were dissolved in 31.5 parts of cold distilled water in a glass mold. The solution was polymerized in the presence of redox catalyst system containing 1.7 parts of each ammonium persulfate and sodium m-bisulfite as described in Example 5.

EXAMPLE 10

35.4 parts of Quadrol dimethacrylate (VII-a) and 1.4 parts of tetraethyleneglycol dimethacrylate were mixed with 70 parts of cold distilled water. The slightly hazy solution was polymerized as described in Example 5 using 2.1 parts of ammonium persulfate as a redox initiator.

EXAMPLE 11

Polymerization of Quadrol methacrylate (VI-a) was carried out in a 50 ml round bottom flask fitted witha mechanical stirrer, a thermometer, a nitrogen inlet, an addition funnel and a drying tube.

10.0 mls of dimethylformamide (dried and distilled over sodium hydride) was brought to 70° C. in a reaction flask under nitrogen atmosphere. 3.2442 g of Quadrol methacrylate (VI-a) and 0.0324 g of N,N'-azobis-(isobutyronitrile) (AIBN) were dissolved in 7 mls of dried DMF in a pressure equalizing addition funnel. This solution was added to the reaction flask with mechanical agitation. The reaction was allowed to proceed at 70° C. for two hours at which time 0.0032 g of AIBN dissolved in 2 mls of DMF was added to the reaction. At the end of additional one hour, polymer was isolated as a clear paste by removal of DMF under reduced pressure.

The polymer was dissolved in 10 mls of a 50:50 mixture of distilled water and methanol. The clear solution was dialyzed against 3000 mls of 50:50 mixture of $H_2O$-$CH_3OH$ using 2000 molecular weight cut-off dialysis tubing. The dialyzing solution was charged every 24 hours over a total dialysis period of 3 days. Finally, the solution was dialyzed against 4000 mls of methanol. The polymer solution was taken out of the tube, filtered and methanol was removed under reduced pressure to yield white shiny polymer. It was dissolved in methylene chloride, dried over magnesium sulfate, filtered and recovered again as a fluffy, very hygroscopic material in 42 percent yield based on monomer weight.

The polymer was readily soluble in chlorinated hydrocarbons, water, dimethylsulfoxide, dimethylacetamide, acetone, methanol, ethanol, tetrahydrofuran and insoluble in toluene, benzene and hexane. Its inherent viscosity (Cannon-Fenske) in tetrachloroethane at 30° C. was 0.10 g./dl (0.5 g/100 ml of solvent). The number average molecular weight of the polymer using a Knauer vapor pressure osmometer was 10,135. Thermogravimetric analysis of the polymer on a Dupont 1090 thermal analyzer indicated a glass transition temperature of 32° C.

EXAMPLE 12

Copper(II) complexation with poly(Quadrol methacrylate) hydrogel(PQM):

Poly(Quadrol methacrylate)(PQM) hydrogel was prepared and exhaustively swelled and dialyzed (Spectropor dialysis tubing, 10,000 MWCO) to remove unreacted monomer. The hydrogel was then treated with increasing concentrations of copper (II) chloride. The absorbance maximum for the Quadrol:Cu complex at 675 nm was monitored following the methods of Hall et al. as described in the *Journal of the American Chemical Society*, vol. 79, page 3361 (1957). Absorbance of a 0.226 millimol solution of quadrol in PQM was found to increase linearly with increasing amounts of 0.1 molar cupric chloride solution until the [$Cu^{++}$]/[Quadrol in PQM] concentration ratio reached about 1.0 (molar ratio). Absorbance then leveled off quickly with further increases in copper ion concentration, and reached a maximum at a [$Cu^{++}$]/[Quadrol in PQM] ratio of 1.5.

EXAMPLE 13

Polymer made in Example 5 was allowed to dissolve in distilled water. The resulting slightly viscus solution was dialyzed against a large volume of phosphate buffered saline (pH 7.2) using 2000 molecular weight cut-off dialysis tubing to remove redox catalysts, unreacted Quadrol methacrylate and low molecular weight oligomers. The biological activity of the buffered poly(Quadrol methacrylate) solution was assayed by measuring in vitro phagocytosis of polystyrene beads following the procedures of M. V. Bhide, et al, *Journal of Immunopharmacology*, vol 7, no. 3 (1985), pp. 303–308. The phagocytosis was found to be 53 percent for control (phosphate buffered saline) and 68 percent for poly(Quadrol methacrylate).

While this invention has been described with reference to specific embodiments thereof, it is apparent that the invention is not limited thereto and that various modifications can be made without departing from the scope of this invention.

The embodiments of the invention in which an exclusinve property or privilege is claimed are defined:

1. A wound dressing containing, as a therapeutically active agent, a hydrogel comprising (a) a cross-linked polymer of a major amount of a compound of the formula (I)

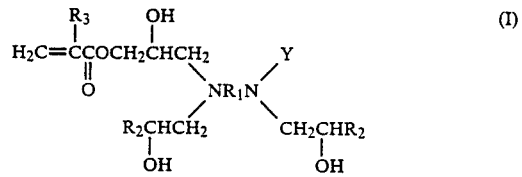

wherein $R_1$ is a divalent hydrocarbon radical containing from 2 to about 6 carbon atoms; $R_2$ is hydrogen, methyl or ethyl; $R_3$ is hydrogen or methyl; and Y is

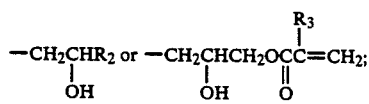

and (b) water.

2. A wound dressing according to claim 1 wherein said polymer is a polymer of a major amount of Quadrol methacrylate or Quadrol dimethacrylate.

3. A wound dressing according to claim 1 wherein Y is

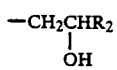

4. A wound dressing according to claim 2 wherein said polymer is a polymer of a major amount of Quadrol monomethacrylate.

5. A wound dressing according to claim 1 wherein said polymer is a polymer of a major amount of said compound of the formula (I) and a minor amount of one or more hydrophilic comonomers.

6. A wound dressing according to claim 1 wherein said hydrogel has an equilibrium water content of at least 80 percent by weight.

* * * * *